United States Patent
Stewart, Jr.

(10) Patent No.: US 6,349,727 B1
(45) Date of Patent: Feb. 26, 2002

(54) PENILE CLAMP FOR INHIBITING INCONTINENCE

(75) Inventor: Edward Stewart, Jr., Dodge City, KS (US)

(73) Assignee: Pos-T-Vac, Inc., Dodge City, KS (US)

(*) Notice: Subject to any disclaimer, the term of this patent is extended or adjusted under 35 U.S.C. 154(b) by 0 days.

(21) Appl. No.: 09/578,557

(22) Filed: May 25, 2000

(51) Int. Cl.[7] ................................................. A61F 5/48
(52) U.S. Cl. ............................... 128/885; 128/DIG. 25; 606/157
(58) Field of Search ......................... 128/DIG. 25, 885, 128/887, 886, 869; 606/151, 157, 206, 207, 201, 203; 24/520, 521; 600/29–31

(56) References Cited

U.S. PATENT DOCUMENTS

| | | |
|---|---|---|
| 678,943 A * | 7/1901 | Davis .......................... 128/883 |
| 1,728,322 A | 9/1929 | Badrian |
| 2,618,270 A | 11/1952 | Pearson, Jr. |
| 2,756,753 A | 7/1956 | Means |
| 3,147,754 A | 9/1964 | Koessler |
| 3,203,421 A | 8/1965 | Bialick |
| 3,598,125 A | 8/1971 | Cogley |
| 3,604,425 A | 9/1971 | Le Roy |
| 3,866,611 A | 2/1975 | Baumrucker |
| 4,106,508 A | 8/1978 | Berlin |
| 4,586,503 A * | 5/1986 | Kirsch et al. ............... 606/155 |
| D299,168 S | 12/1988 | Bergstrom et al. |
| 4,880,016 A | 11/1989 | Worth et al. |
| 4,942,886 A * | 7/1990 | Timmons ..................... 128/885 |
| 5,336,157 A * | 8/1994 | Hale ............................ 604/41 |
| 5,462,555 A * | 10/1995 | Bolanos et al. ............. 606/120 |
| 5,515,872 A * | 5/1996 | Martin et al. ............... 128/898 |
| 5,571,125 A | 11/1996 | Chadwick |
| 5,693,060 A | 12/1997 | Martin |

FOREIGN PATENT DOCUMENTS

DE       2545477 A1 *   4/1977

* cited by examiner

*Primary Examiner*—Kennedy Schaetzle
*Assistant Examiner*—Kristen Droesch
(74) *Attorney, Agent, or Firm*—Hovey, Williams, Timmons & Collins

(57) ABSTRACT

A penile clamp for inhibiting male incontinence is provided as a single, unitary, synthetic resin body having a pair of jaw-like arms, a bridge interconnecting the arms and biasing them to a penis clamping position, and a pair of ears. The ears may be pinched together to spread apart the arms, thereby permitting insertion of a penis between the arms. One of the arms includes a penis-cradling area which is concave to conform to the top of the penis, while the other arm includes a urethral pressuring area which is preferably convex to apply pressure directly against the underside of the penis outside of the urethra. The pressuring area may be either a cantilever spring extending toward the bridge from the remote end of the second arm, or an area of the second arm between its proximate and remote ends. The arms are connected to the bridge at their proximate ends and presenting an opening across from the bridge opposite their remote ends. The penis-cradling area is preferably relatively wide in comparison to the pressure applying area which is relatively narrow and thus reduces the amount of compressive force which is provided to the arms to clamp the urethra closed at one point therealong and inhibit the undesired flow of urine therepast. The user may selectively urinate in a discrete and private manner simply by pinching together the ears to spread the arms and relieve pressure on the urethra.

21 Claims, 2 Drawing Sheets

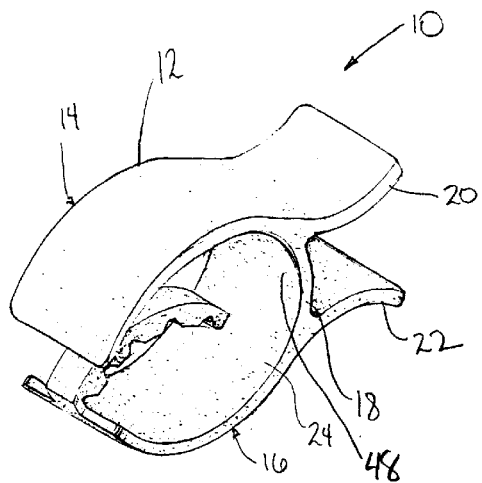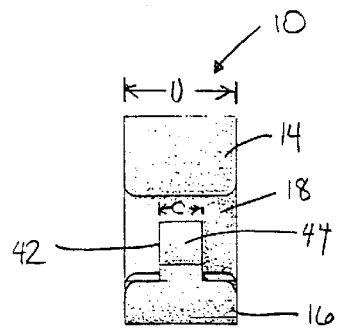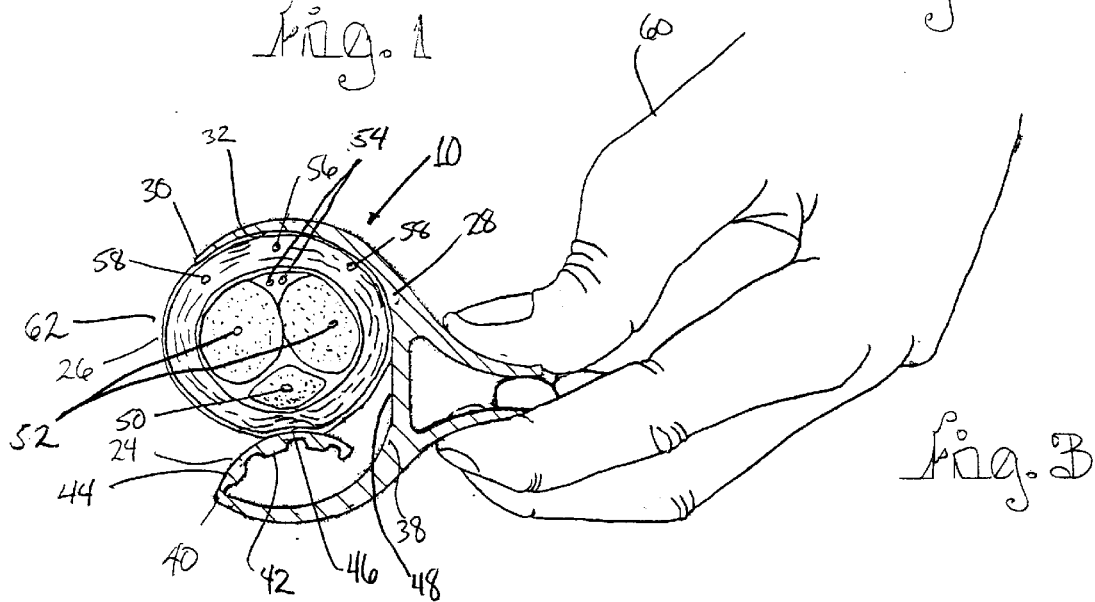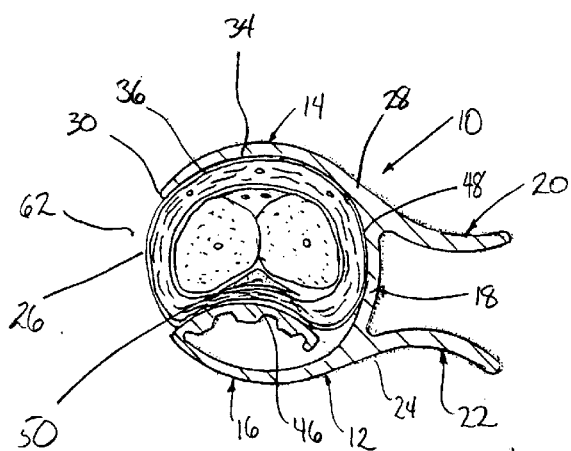

PENILE CLAMP FOR INHIBITING INCONTINENCE

BACKGROUND OF THE INVENTION

1. Field of the Invention

This invention concerns a clamp for application to a penis which applies pressure to the urethra to block the undesired flow of urine therepast. More particularly, it is concerned with a compact, unitary clamp which may be worn during everyday activities and having a pair of ears opposite a side opening whereby the ears may be pinched to widen a corresponding pair of arms for sliding the clamp over the penis, whereupon the ears may be released to apply pressure to the penis specifically to the urethra.

2. Description of the Prior Art

Incontinence is a problem encountered by many men and is more common among geriatrics. While the cause of male incontinence may have a variety of different reasons, the uncontrolled and undesired passage of urine is a significant problem resulting in embarrassment and restriction of activities. While adult diapers are one solution to the problem, they are bulky, retain the moisture, and are embarrassing and difficult for some aging men to handle in public lavatories.

Other devices have been developed over the years, but are more suited to invalids or overnight use due to their bulky characteristics and often difficult for a user to manage. Such devices include those shown and described, for example, in U.S. Patents D 299,168 to Bergstrom et al.; U.S. Pat. No. 1,728,322 to Badrian; U.S. Pat. No. 2,756,753 to Means; U.S. Pat. No. 3,147,754 to Koessler; U.S. Pat. No. 3,203,421 to Balick; U.S. Pat. No. 3,866,611 to Bamrucker; U.S. Pat. No. 4,880,016 to Worth, et al.; U.S. Pat. No. 4,942,886 to Timmons; and U.S. Pat. No. 5,571,125 to Chadwick.

There has developed a need for an improved male incontinence control which may be carried by the penis during everyday activities of the user, is easy for older men to use, and provides control of incontinence without causing necrosis of the penile tissue.

SUMMARY OF THE INVENTION

These needs have largely been met by the penile clamp of the present invention. In addition to being economical to produce, the device is simple to understand and apply, is both comfortable and compact to permit usage in everyday situations outside the home, resists shifting on the penis which might occlude blood flow, and may be relaxed to permit desired urination by the user without the necessity of removal. This last feature is of great benefit to many men, as it permits them to urinate in a normal manner, such as standing vertically at a urinal, and thereby enhances and retains their self-image and esteem.

Broadly speaking, the clamp of the present invention includes a unitary member formed of synthetic resin which is flexible but sufficiently hard to avoid deformation of the surface of the device. The clamp includes two arms which are designed to envelop a section of the penis. A bridge section connects the two arms, with two ears extending from the bridge section opposite the arms. The arms are thus connected to and integral with the bridge and the ears at a proximate end, but have an opening between their distal ends. This opening enables the ears to be pinched together by one hand to open the arms, which are resilient and normally biased to clamp onto the penis. One of the arms has a concave inner surface to substantially conform around the top side of the users penis. The other arm has an arcuate member which is convex in the area of the urethra to impart a clamping force thereon. In one embodiment, the arcuate member extends in the manner of a cantilevered spring from the distal end of the other arm toward the bridge. In another embodiment, the arcuate member is formed on the lower arm itself. Preferably, the arcuate member is narrowed in width relative to the bridge and upper arm, whereby its clamping force may be focused on only a relative narrow portion of the urethra to provide a point blockage therein. Also, all or a portion of the clamp has a fabric or flocked surface which absorbs moisture and inhibits longitudinal or circumferential slippage of the clamp. The flocked surface improves comfort for the user and because it inhibits slippage, not only improves the performance of the device but resists movement which could cause the arcuate member to shift opposite a vein or artery in the penis.

These and other features of the penile clamp hereof will be readily apparent to those skilled in the art with reference to the drawings and description which follow.

BRIEF DESCRIPTION OF THE DRAWINGS

FIG. 1 is a perspective view of a first embodiment of the penile clamp of the present invention having a cantilever spring blocking member and showing the flocked coating applied thereon;

FIG. 2 is an end elevational view thereof showing the upper and lower arms of the clamp and the cantilever spring blocking member extending inwardly from the remote end of the lower arm;

FIG. 3 is a vertical cross-sectional view of a penis and the clamp of FIG. 1 showing the user pinching together the ears of the clamp open the arms sufficiently to permit either placement of the clamp on the penis or urination;

FIG. 4 is a cross-sectional view of a penis and the clamp similar to FIG. 3, showing the arms biased to their normal urethral-blocking position;

DESCRIPTION OF THE PREFERRED EMBODIMENT

Figure 5:
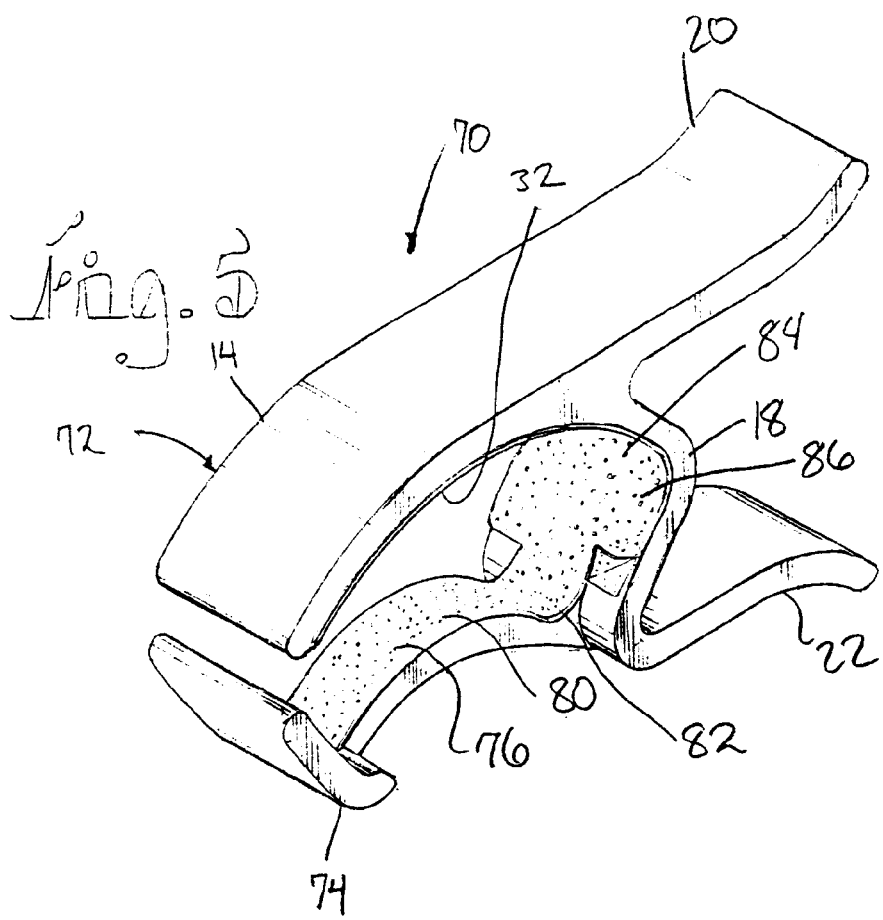
FIG. 5 is a perspective view of a second embodiment of penile clamp of the present invention showing a clamp having its lower arm including a convex urethral pressuring stretch of narrowed width and a remote support area of relatively wider width.

Referring now to the drawings, a penile clamp 10 for inhibiting male incontinence in accordance with a first embodiment of the invention hereof is shown in FIGS. 1 through 4. The penile clamp 10 is preferably molded of a substantially hard, resilient, synthetic resin, having a flex modulus reading of between 3.70 and 3.80 and a notched Izod Impact rating of between 1.0 and 1.5. One such resin which has the desired hardness and resiliency is a thermoplastic such as Celcom C-9 Acetal by Ticona.

The clamp 10 includes a body 12 including a first, upper arm 14, a second, lower arm 16, a bridge 18 interconnecting the arms 14 and 16 and biasing them toward a clamping position as shown in FIG. 4, a first ear 20 extending from the bridge 18 opposite the first arm 14, and a second ear 22 extending from the bridge 18 opposite the second arm and in opposed relationship to the first ear 20. A fabric or flocked coating 24 may be applied to selected portions or, as illustrated in FIG. 1, the entire surface of the body 12, which provides a combination of cushioning, water absorbency, promotes slip resistance by providing greater friction between the clamp 10 and the penis 26, and particularly when the flocking is white, shows soiling.

In greater detail, the first, upper arm 14 has a proximate end 28 comuected to the bridge 18, a free, remote end 30, and a concave inner surface 32 providing a penis-cradling area 34. As shown in FIGS. 3 and 4, the upper side 36 of the penis 26 is rounded. The penis-cradling area 34 of the upper arm 14 has a width U which is relatively wide, and thus spreads the force imparted to the upper side 36 of the penis 26 by the clamp 10 to a relatively wide area without concentrating the force in any narrowed area.

The second, lower arm 16 has a proximate end 38 connected to the bridge 18, and a free, remote end 40. The portion of the second arm extending between the proximate end 38 and the remote end 40 may have a width substantially the same as the width U of the upper arm in the penis cradling area 34. However, the second arm 16 also includes a relatively narrow cantilever spring member 42 which extends inwardly toward bridge 18 from the remote end 40. The cantilever spring member 42 has a convex inner surface 44 facing the concave inner surface 32 of the upper arm 14 presenting a urethral pressuring area 46 thereon. Preferably, at least this urethral pressuring area 46, and most preferably all of the cantilever spring member 42, is of a substantially narrower width C than the width U of the penis-cradling area 34. Thus, as it is undesirable to press against areas other than as necessary to block the flow of urine through the urethra, the force provided by the lower arm 16 is concentrated into a narrow width and is greatest at the pressuring area 46 located approximately in the middle of the convex inner surface 44 of the cantilever spring member 42.

The bridge 18 is molded to comfortably receive the penis 26 by its complementally configured interior surface 48 and by spacing the arms 14 and 16 the desired distance to permit clamping on the urethra 50 without acting as a tourniquet to block the flow of blood through the profunda arteries 52, the dorsal arteries 54, the subcutaneous dorsal vein 56, and the subcutaneous lateral dorsal veins 58. Thus, the bridge 18 biases the upper and lower arms 14 and 16 into a clamping position as shown in FIG. 4.

The first ear 20 extends from the bridge 18 opposite from the upper arm 14. The second ear 22 extends from the bridge 18 opposite from the lower arm 16 and in spaced and opposed relationship to the first ear 20. The outer surfaces of the ears 20 and 22 are flat or slightly concave as shown in FIG. 4 to provide a good grasping surface for the user to place his thumb and forefinger. The bridge 18 acts as a spring and, to an extent, a hinge, with the movement of first car 20 resulting in corresponding movement of arm 14 and movement of second ear 22 resulting in corresponding movement of arm 16. Because the body is integrally formed, when the user 60 presses or pinches the ears 20 and 22 toward one another as shown in FIG. 3, as the ears close toward one another, the arms 14 and 16 spread or diverge, as their remote ends are free and unconnected, presenting an opening 62 opposite the bridge 18. Thus, by pressing the ears 20 and 22 together, their respective arms 14 and 16 spread apart at opening 62 to enable the clamp 10 to be inserted laterally at the desired location along tile penis. While the force required to fully open the opening 62 with the ears 20 and 22 is well within the capability of many elderly men, requiring only about 12 pounds, less force is applied to the urethra as the arms 14 and 16 are only slightly spread when the penis 26 is therebetween as shown in FIG. 4, and the cantilever spring member 42 is narrower than the bridge 18 and the remainder of the second arm 16 so that less force is needed to deflect it while maintaining sufficient force (about 12 to 14 ounces) on the urethra to maintain it closed. When the ears 20 and 22 are released, the bridge 18 biases the arms 14 and 16 into a clamping position as shown in FIG. 4 with the pressuring area 46 closing the urethra to block the flow of urine therepast. One particularly useful material for the coating 24, which is preferably a sprayed-on fiber coating having a quick drying adhesive, is rayon, but other cloth or fiber materials or rubber-like coatings which promote increased friction between the clamp 10 and the penis 26 may be employed to inhibit slippage of the clamp 10 along the penis and cushion the application of force to the penis by the arms.

Figure 6:
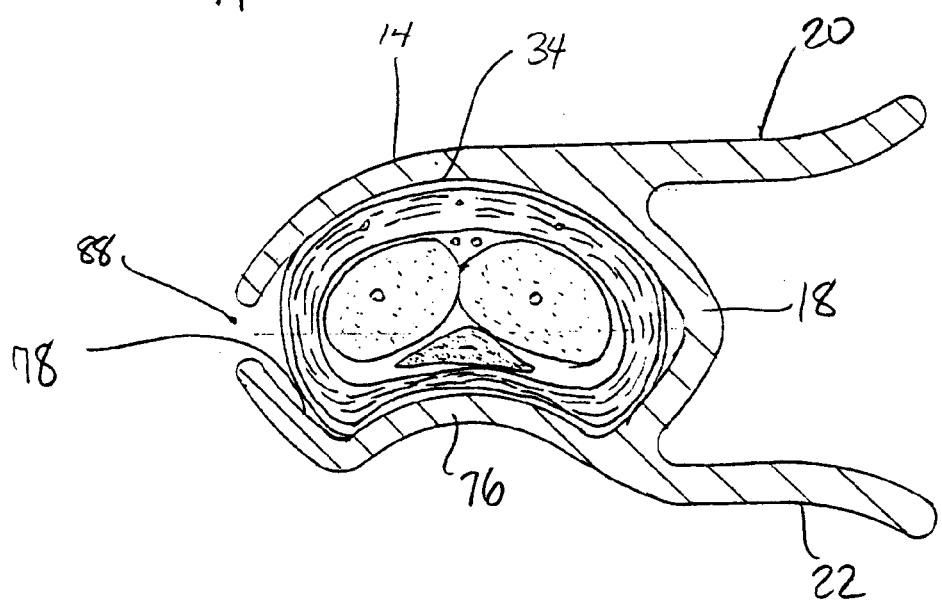
FIG. 6 is a vertical cross-sectional thereof, showing the upper and lower arms in a urethral clamping position.

Clamp 70 shown in FIGS. 5 and 6 is similar to clamp 10 shown in FIGS. 1 through 4 in that it has a first, upper arm 14, bridge 18, and first ear 20 and second ear 22 the same as described above. However, the body 72 of clamp 70 has a second, lower arm 74 which extends from the bridge 18 and includes a urethral pressuring section 76 and a support area 78. The support area 78 has a relatively wide width approximately the same as width U of the upper arm, while urethral pressuring section 76 has an convex inner surface 80 and a narrowed width W which is substantially the same as width C. The urethral pressuring section 76 is thus opposite the penis-cradling area 34. A coating 82 of resilient material such as the flocked coating 24, natural or synthetic rubber is applied to only a portion 84 of the surface of the clamp 70 along the convex inner surface 80, the inner wall 86 of bridge 18, and the concave inner surface 32 of upper arm 14 as shown in FIG. 5. The ears 20 and 22 may be pinched or pressed together to admit the penis between upper arm 14 and lower arm 72 through opening 88. When the ears 20 and 22 are released, the bridge 18 biases the arms 14 and 72 to their normal, clamping position as shown in FIG. 6.

It may thus be appreciated that the clamps 10 and 70 offer substantial advantages and improvements over the prior art. Not only are they simple and economical to make, but they are simply to apply and use without any assistance. This is especially important for older men who value their dignity and resent the need for others to assist in the private act of controlling urination. The clamps 10 and 70 may be worn in all daily activities without requiring alterations in ones wardrobe. The clamping force is sufficiently low and concentrated only in the needed area to minimize any tissue damage or discomfort. The body of the clamp is small, with the opposing arms occupying little additional space and the ears being relatively short (preferably extending less than 1" from the bridge) and so the clamp is hardly noticeable when worn under trousers. In order for the user to urinate in a standing position at a urinal, the act appears to others as being of little different than ordinary urination, with the user simply positioning his penis and then pinching together the ears 20 and 22 to remove pressure against the urethra and permit urine to flow therethrough. The coating helps not only in providing cushioning and absorbency, but also to resist shifting of the clamps 10 and 70, so that the clamps may remain in place without the need for reinstallation on a repeated basis. After the urination is complete, the user simply relaxes the pinching action on the ears and permits the upper and lower arms to close around the penis 26.

Although preferred forms of the invention have been described above, it is to be recognized that such disclosure is by way of illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventor hereby states his intent to rely on the Doctrine of Equivalents to determine and assess the reasonably fair scope of his invention as pertains to any apparatus not materially departing from but outside the literal scope of the invention as set out in the following claims.

What is claimed is:

1. A penile clamp for inhibiting male incontinence comprising:

a first arm member having a remote end, a proximate end and a concave inner surface for cradling therein a penis;

a second arm member having a remote end, a proximate end and a convex inner surface for engaging a penis directly opposite the first arm member;

a bridge interconnecting the first and second arm members at their respective proximate ends, the bridge spacing the proximate ends of the first and second arm members and having an arcuate interior surface complementally configured for receiving a man's penis, said bridge biasing the first and second arm members to a penis-clamping position and positioning the concave surface of the first arm member in direct opposition to the convex surface of the second arm member in spaced relationship to receive a man's penis therebetween;

a first ear member extending from the bridge opposite the first arm member and connected thereto;

a second ear member extending from the bridge opposite the second arm member and connected thereto and in opposed, spaced relationship to the first ear member, whereby pinching of the first and second ears towards one another causes the remote ends and the respective concave and convex inner surface of the first and second arm members to diverge from the penis-clamping position sufficiently to permit insertion of a man's penis between the concave surface and the convex surface.

2. A penile clamp for inhibiting male incontinence as set forth in claim 1, wherein said first and second arms, said first and second ears, and said bridge are integrally formed of a resilient synthetic resin material.

3. A penile clamp for inhibiting male incontinence as set forth in claim 1, wherein at least a portion of one of said inner surfaces of said first and second arms of said clamp is provided with a friction-promoting coating.

4. A penile clamp as set forth in claim 3, wherein substantially the entire clamp is provided with a friction-promoting coating.

5. A penile clamp as set forth in claim 3, wherein the friction promoting coating is water absorbent.

6. A penile clamp as set forth in claim 1, wherein said second arm includes a cantilever spring member connected to and extending from the remote end of said second arm toward the bridge, wherein said convex inner surface is provided on said cantilever spring member which biases said convex inner surface towards said concave inner surface.

7. A penile clamp as set forth in claim 6, wherein said first arm includes a cradling area of a first width and said cantilever spring member has a urethral pressuring area of a second width substantially narrower than the first width.

8. A penile clamp for inhibiting male incontinence comprising:

a first arm member having a remote end, a proximate end and a concave inner surface for cradling therein a penis;

a second arm member having a remote end, a proximate end and a convex inner surface for engaging a penis opposite the first arm member;

a bridge interconnecting the first and second arm members at their respective proximate ends and biasing them to a penis-clamping position;

a first ear member extending from the bridge opposite the first arm member and connected thereto;

a second ear member extending from the bridge opposite the second arm member and connected thereto and in opposed, spaced relationship to the first ear member, whereby pinching of the first and second ears towards one another causes the remote ends and the respective concave and convex inner surface of the first and second arm members to diverge from the penis-clamping position; and a cradling area of a first width on said first arm, wherein said convex inner surface on said second arm has a urethral pressuring area of a second width substantially narrower than said first width.

9. A penile clamp as set forth in claim 8, wherein said second arm includes a support area adjacent the remote end thereof, said remote end having a width substantially greater than the width of the urethral pressuring area.

10. A penile clamp as set forth in claim 9, wherein the width of the support area is substantially the same as the width of the cradling area of the first arm.

11. A penile clamp for inhibiting male incontinence comprising a unitary, integrally formed, resilient synthetic resin body having a first arm presenting a proximate end and a remote end and a concave inner surface thereon, a second arm presenting a proximate end and a remote end and a convex inner surface located in direct opposition to the concave surface, a bridge interconnecting the proximate ends of the first and second arms and biasing the arms toward one another with said remote ends of the first and second arms positioned in spaced relationship, a first ear connected to said bridge and extending substantially opposite to said first arm, and a second ear connected to said bridge and extending substantially opposite to said first arm in opposed, facing relationship to said first ear.

12. A penile clamp for inhibiting male incontinence comprising:

a first arm member presenting a penile cradling area of a first, relatively wide width;

a second arm member positioned in opposition said first arm member and having a urethral pressuring area of a second, relatively narrow width opposite the cradling area;

a bridge connecting the first and second arm members and biasing them into a position wherein a penis positioned therebetween is clamped between said cradling area and said pressuring area; and first and second ears respectively operatively connected to said first and second arm members for selectively increasing the distance between the cradling area and the pressuring area.

13. A penile clamp as set forth in claim 12, wherein said urethral pressuring area is arcuate and convex in the direction facing the penile cradling area of the first arm member.

14. A penile clamp as set forth in claim 13, wherein said second arm has a proximate end and a remote end and said urethral pressuring area is positioned intermediate said proximate end and said remote end.

15. A penile clamp as set forth in claim 14, wherein said second arm includes a support area having a wider width relative to said urethral pressuring area and positioned on said second arm remote from said urethral pressuring area.

16. A penile clamp as set forth in claim 13, wherein said second arm has a proximate end and a remote end, and said urethral pressuring area extends from said remote end inwardly toward said bridge.

17. A penile clamp as set forth in claim 12, wherein at least a portion of one of said penile cradling area and urethral clamping area is covered by a resilient material.

18. A penile clamp as set forth in claim 17, wherein said resilient material promotes frictional engagement between the clamp and the skin of the penis.

19. A penile clamp as set forth in claim 12, wherein said first arm member, second arm member, bridge, and first and second ears are integrally formed of resilient synthetic resin material.

20. A method of inhibiting male incontinence, comprising the steps of:
  providing a clamp presenting first and second arms having respective penile cradling and urethral pressuring areas thereon, a connector biasing the cradling and pressuring areas of the arms together and a pair of ears operatively connected to the first and second arms for spreading the arms;
  actuating the ears to spread the first and second arms away from one another;
  inserting a penis into the clamp whereby the urethra of the penis is positioned adjacent the urethral pressuring area of the second arm;
  blocking the flow of urine through the urethra by permitting the connector to bias the first and second arms together with the penile cradling area of the first arm cradling the upper side of the penis and the urethral pressuring area of the second arm positioned to concentrate pressure along the urethra on the underside of the penis;
  selectively actuating the ears to spread the first and second arms away from one another and reduce the pressure applied to the urethra without removing the clamp from the penis to permit urination.

21. A penile clamp for inhibiting male incontinence comprising:
  a first arm member having a concave inner surface for cradling therein a penis;
  a second arm member having a convex inner surface for engaging a penis opposite the first arm member;
  a bridge interconnecting the first and second arm members at their respective proximate ends and biasing them to a penis-clamping position;
  a first ear member extending from the bridge opposite the first arm member and connected thereto;
  a second ear member extending from the bridge opposite the second arm member and connected thereto and in opposed, spaced relationship to the first ear member, whereby pinching of the first and second ears towards one another causes the remote ends and the respective concave and convex inner surface of the first and second arm members to diverge from the penis-clamping position; and
  a water-absorbent friction-promoting coating provided on at least a portion of one of said inner surfaces of said first and second arms.

* * * * *